United States Patent [19]
Yarosh

[11] Patent Number: 5,077,211
[45] Date of Patent: Dec. 31, 1991

[54] PURIFICATION AND ADMINISTRATION OF DNA REPAIR ENZYMES

[75] Inventor: Daniel B. Yarosh, Merrick, N.Y.

[73] Assignee: Applied Genetics, Inc., Freeport, N.Y.

[21] Appl. No.: 215,566

[22] Filed: Jul. 6, 1988

[51] Int. Cl.$^5$ .................. C12N 9/10; C12N 9/16; A61K 37/52; A61K 37/54
[52] U.S. Cl. ........................ 435/193; 435/196; 435/199; 424/94.5; 424/94.6; 424/450
[58] Field of Search ............... 435/196, 193; 424/94.5, 424/94.6, 450

[56] References Cited

U.S. PATENT DOCUMENTS

| | | | |
|---|---|---|---|
| 4,356,167 | 10/1982 | Kelly | 424/38 |
| 4,789,633 | 12/1988 | Huang et al. | 435/240.2 |

FOREIGN PATENT DOCUMENTS

WO90/00598  1/1990  PCT Int'l Appl.

OTHER PUBLICATIONS

Myrnes et al., *Eur. J. Biochem.*, vol. 173, No. 2, pp. 383–387, 1988.
Michael Mezei and Vijeyalakshmi Gulasekharam, Life Sciences, vol. 26, pp. 1473–1477, 1980.
Michael Mezei and Vijeyalakshmi Gulasekharam, Journal of Pharmacy and Pharmacology, vol. 34, pp. 473–474, 1981.
Adrienn Gesztes and Michael Mezei, Anesthesia and Analgesia, vol. 67, pp. 1079–1081, 1988.
H. M. Patel, Biochemical Society Transactions, vol. 13, pp. 513–516, 1985.
W. Wohlrab and J. Lasch, Dermatologica, vol. 174, pp. 18–22, 1987.
Robert Straubinger, Keelung Hong, Daniel Friend and Demetrios Papahadjopoulos, Cell, vol. 32, pp. 1069–1079, 1983.
Robert Straubinger, Nejat Duzgunes and Demetrios Papahadjopoulos, FEBS Letters, vol. 179, pp. 148–154, 1985.
Chaper 11 of the book Cell Fusion, edited by A. E. Sowers, Plenum Press, N.Y., 1987, pp. 241–267.
Ellens, Bentz and Szoka, Biochemistry, vol. 23, pp. 1532–1538, 1984.
Bentz, Ellens and Szoka, Biochemistry, vol. 26, pp. 2105–2116, 1987.
Ganesan, et al., *International Journal of Pharmaceutics*, vol. 20, pp. 139–154, 1984.
Ho, et al., *Journal of Controlled Release*, vol. 2, pp. 61–65, 1985.
Jacobs, et al., *J. Pharm. Pharmacol.*, vol. 40, pp. 829–833, 1988.
Komatsu, et al., *Chem. Pharm. Bull.*, vol. 34, pp. 3415–3422, 1986.

(List continued on next page.)

*Primary Examiner*—Elizabeth C. Weimar
*Assistant Examiner*—Charles L. Patterson, Jr.
*Attorney, Agent, or Firm*—Maurice M. Klee

[57] ABSTRACT

Methods for purifying DNA repair enzymes are provided in which an aqueous solution of a DNA repair enzyme in an impure state is applied to a molecular sieve column having an exclusion limit which will retard the DNA repair enzyme but will not retard contaminants larger than the DNA repair enzyme. The DNA repair enzyme in an enhanced state of purity is eluted isocratically from the molecular sieve column in an elution buffer and applied directly to a DNA affinity column in the same buffer without intermediate dialysis, ultrafiltration, or other procedures. The DNA repair enzyme is eluted from the DNA affinity column using, for example, a salt gradient. The method is rapid, inexpensive, simple to perform, and has been found to produce a homogeneous final product. In accordance with other aspects of the invention, the purified DNA repair enzymes are encapsulated in liposomes and administered to living cells in situ. This form of administration has been found to be non-toxic to the cells and to result in increased incision of damaged DNA, enhanced DNA repair synthesis, and increased cell survival after exposure to ultraviolet light.

25 Claims, 1 Drawing Sheet

OTHER PUBLICATIONS

Shek, et al., *Biochimica et Biophysica Acta*, vol. 902, pp. 229–236, 1987.

Strauss, G., *J. Soc. Cosmet. Chem.*, vol. 40, pp. 51–60, 1989.

Vermorken, et al., *J. Pharm. Pharmacol.*, vol. 36, pp. 334–336, 1984.

Westerhof, W., *Medical Hypotheses*, vol. 16, pp. 283–288, 1985.

*Liposome Technology*, edited by G. Gregoriadis, 1984, published by CRC Press, Boca Raton, Florida, vol. II, Chapter 12, pp. 177–185.

*Liposome Technology*, edited by G. Gregoriadis, 1984, published by CRC Press, Boca Raton, Florida, vol. II, Chapter 15, pp. 207–221.

*Repair of DNA Lesions Introduced by N-Nitroso Compounds*, B. Myrnes & H. Krokan eds., Norwegian Univ. Press, Oslo, 1986, pp. 112–134.

Yamaizumi et al., *Mutation Research*, vol. 217, pp. 135–140, 1989.

Chenevert et al., Molecular and General Genetics, 1986, vol. 203, pp. 163–171.

Ciarrocchi et al., Proceedings of the National Academy of Sciences U.S.A., 1978, vol. 75, pp. 1887–1891.

Demple et al., The Journal of Biological Chemsitry, vol. 257, pp. 13776–13780, 1982.

Freeman et al., Analytical Biochemistry, vol. 158, pp. 119–129, 1986.

Friedberg et al., Journal of Bacteriology, 1971, vol. 106, pp. 500–507.

Higgins et al., Mutation Research, 1987, vol. 183, pp. 117–121.

Hoeijmakers, Journal of Cell Science Suppl., 1987, vol. 6, pp. 111–125.

McMillan et al., Journal of Virology, 1981, vol. 40, pp. 211–223.

Mosmann, Journal of Immunological Methods, vol. 65, pp. 55–63, 1983.

Myrnes et al., Carcinogenesis, 1984, vol. 5, pp. 1061–1064.

Nakabeppu et al., The Journal of Biological Chemistry, vol. 260, pp. 7281–7288, 1985.

Nakabeppu et al., Proceedings of the National Academy of Sciences, 1981, vol. 78, pp. 2742–2746.

Nakabeppu et al., Journal of Biological Chemistry, 1982, vol. 257, pp. 2556–2562.

Ostro, "Liposomes", Scientific American, Jan. 1987, vol. 256, pp. 2–11.

Robbins et al., Annals of Internal Medicine, vol. 80, No. 2, pp. 221–248, Feb., 1974.

Seawell et al., in DNA Repair, edited by Friedberg et al., NY, 1981, vol. 1, Part A, pp. 229–236.

Tanaka et al., Proceedings of the National Academy of Sciences, U.S.A., 1977, vol. 74, pp. 2958–2962.

Tanaka et al., Proceedings of the National Academy of Sciences U.S.A., 1975, vol. 72, pp. 4071–4075.

Valerie et al., Cancer Research, 1987, vol. 47, pp. 2967–2971.

Warner et al., Journal of Virology, 1981, vol. 40, pp. 204–210.

Yarosh, Mutation Research, vol. 145, pp. 1–16, 1985.

Yarosh et al., Molecular and Cellular Biology, 1981, vol. 1, pp. 237–244.

Yasuda et al., Proceedings of the National Academy of Sciences, Dec., 1970, vol. 67, pp. 1839–1845.

Yasuda et al., Biochimica et Biophysica Acta, 1976, vol. 442, pp. 197–207.

DNA Repair, edited by Friedberg et al., vol. I, Part A, Chapters 18, 20–22; vol. II, Chapters 3–5; vol. III, Section IV, Chapters 23–25.

PURIFICATION AND ADMINISTRATION OF DNA REPAIR ENZYMES

BACKGROUND OF THE INVENTION

1 Field of the Invention

This invention relates to DNA repair enzymes and, in particular, to 1) methods for purifying DNA repair enzymes, and 2) methods and means for administering DNA repair enzymes to living cells in situ, e.g. human skin cells, so that the enzymes can enter the cells and enhance the repair of damaged DNA in the cells.

2. Description of the Prior Art

Skin cancer is a serious human health problem. The incidence of non-melanoma skin cancer in the United States is 500,000 per year, and 23,000 per year for melanoma. Annual deaths are 2,000 and 6,000 respectively, and 800,000 deaths from skin cancer are predicted in the next 88 years if current trends continue.

The causal link between non-melanoma skin cancer and ultraviolet light exposure from the sun has been clearly established, and sun exposure is an important causative factor in melanoma. The target for ultraviolet light damage leading to cancer is widely accepted as DNA.

*Xeroderma pigmentosum* is a human genetic disease in which patients develop solar damage, pigmentation abnormalities and malignancies in sun-exposed skin. A review of the disease was authored by J. H. Robbins, K. H. Kraemer, M. A. Lutzner, B. W. Festoff and H. G. Coon, entitled "*Xeroderma Pigmentosum:* An Inherited Disease with Sun Sensitivity, Multiple Cutaneous Neoplasms, and Abnormal DNA Repair", and published in the *ANNALS OF INTERNAL MEDICINE*, volume 80, number 2, pages 221-248, February, 1974. The disease occurs in 1 of 250,000 worldwide. Cells from xeroderma pigmentosum patients are deficient in repair of ultraviolet damage to DNA, which results in a cancer incidence 4,800 times the frequency of the general U.S. population. There is no cure, and treatment consists of avoiding sun exposure and excising skin lesions. Death occurs 30 years earlier in these patients than among the general U.S. population.

Research into the basic mechanisms of DNA repair has established outlines of biochemical pathways which remove ultraviolet damage in DNA. Bacterial repair systems have been demonstrated to differ significantly from repair in human cells. However, the enzyme endonuclease V (also referred to herein as T4 endonuclease V and denV endonuclease V) has the ability to enhance DNA repair in human cells as evidenced by increased UV-specific incision of cellular DNA, increased DNA repair replication, and increased UV survival after treatment with the enzyme.

The endonuclease V enzyme is produced by the denV gene of the bacteriophage T4. It has been established that this enzyme catalyzes the rate limiting, first step in the removal of UV-induced DNA damage, namely, single strand incision of DNA at the site of damage. In particular, the enzyme exhibits glycosylase and apurinic/apyrimidinic endonuclease activities and acts at the site of ultraviolet induced pyrimidine dimers. See "Evidence that the UV Endonuclease Activity Induced by Bacteriophage T4 Contains Both Pyrimidine Dimer-DNA Glycosylase and Apyrimidinic/Apurinic Endonuclease Activities in the Enzyme Molecule" by H. R. Warner, L. M. Christensen and M. L. Persson, in *JOURNAL OF VIROLOGY*, 1981, Vol. 40, pages 204-210; "denV Gene of Bacteriophage T4 Codes for Both Pyrimidine Dimer DNA Glycosylase and Apyrimidinic Endonuclease Activities" by S. McMillan, H. J. Edenberg, E. H. Radany, R. C. Friedberg and E. C. Friedberg, in JOURNAL OF VIROLOGY, 1981, Vol. 40, pages 211-223, and "Physical Association of Pyrimidine Dimer DNA Glycosylase and Apurinic-/Apyrimidinic DNA Endonuclease Essential for Repair of Ultraviolet-damaged DNA" by Y. Nakabeppu and M. Sekiguchi, in *PROCEEDINGS OF THE NATIONAL ACADEMY OF SCIENCES*, 1981, Vol. 78, pages 2742-2746.

Other enzyme having the ability to repair DNA damage have also been identified. These enzymes include $O^6$-methylguanine-DNA methyltransferases, photolyases, uracil- and hypoxanthine-DNA glycosylases, apyrimidinic/apurinic endonucleases, DNA exonucleases, damaged-bases glycosylases (e.g., 3-methyladenine-DNA glycosylase), correndonucleases alone or in complexes (e.g., *E. coli* uvrA/uvrB/uvrC endonuclease complex), and other enzymes and enzyme complexes whose activities at present are only partially understood, such as, the products of the ERCC genes of humans and the RAD genes of yeast. Various of these enzymes have been purified to homogeneity from microorganisms, and the genes for some of the enzymes have been cloned. As used herein, the term "DNA repair enzymes is intended to include the foregoing enzymes, the T4 endonuclease V enzyme, and other enzymes now known or subsequently discovered or developed which have the ability to participate in repair of damaged nucleic acids and, in particular, damaged DNA.

To date, the use of exogenous enzymes in DNA repair systems has been limited to laboratory experiments designed to study the biochemical and evolutionary relationships among DNA repair pathways. Clinical application of these laboratory results has not been undertaken because, inter alia, there has been no effective way of purifying commercial quantities of DNA repair enzymes, and there has been no effective, nontoxic way of administering DNA repair enzymes to living cells. The present invention addresses both of these long-standing problems in the art.

Purification of DNA enzymes for commercial use requires a homogenous final product, high yield, speed, simplicity and low cost. The existing methods of the art have been unable to meet these goals, as follows:

(1) P. Seawell, E. C. Friedberg, A. K. Ganesan and P. C. Hanawalt, "Purification of Endonuclease V of Bacteriophage T4" in *DNA REPAIR: A LABORATORY MANUAL OF RESEARCH PROCEDURES*, edited by E. C. Friedberg and P. C. Hanawalt, Marcel Dekker, Inc., N.Y., 1981, Volume 1, Part A, pages 229-236.

This method uses phage T4 infected *E. coli*, and purification relies on phase-separation and two ion-exchange chromatography steps (DEAE- and phosphocellulose). The DEAE chromatography step limits the yield of the method because all proteins must bind in order to elute the enzyme of interest. The method is not rapid: each chromatography step is preceded by dialysis, each elution requires at least 20 hours, and each fraction is assayed for activity. The process is neither simple nor inexpensive: tedious phase separation and repetitive assays are performed, and all spent dialysate and separated phases are discarded. Significantly, the authors of this method describe their final product as being only partially purified.

The basic steps of the Seawell et al. method were first described by E. C. Friedberg and J. J. King in "Dark Repair of Ultraviolet-irradiated Deoxyribonucleic acid by Bacteriophage T4: Purification and Characterization of a Dimer-Specific Phage-Induced Endonuclease", *JOURNAL OF BACTERIOLOGY*, 1971, Vol. 106, pages 500-507. This earlier version of the method included an additional DNA-cellulose step, which was omitted in the later version. A method similar to the Friedberg and King method was described by S. Yasuda and M. Sekiguchi, "T4 Endonuclease Involved in Repair of DNA" *PROCEEDINGS OF THE NATIONAL ACADEMY OF SCIENCES*, Dec., 1970, Vol. 67, pages 1839-1845. Instead of using a DNA-cellulose step as in the Friedberg and King method, the Yasuda and Sekiguchi method included an optional gel filtration step.

(2) Y. Nakabeppu, K. Yamashita and M. Sekiguchi, "Purification and Characterization of Normal and Mutant Forms of T4 Endonuclease V" *JOURNAL OF BIOLOGICAL CHEMISTRY*, 1982, Vol. 257, pages 2556-2562.

The basic steps of this method were first described by S. Yasuda and M. Sekiguchi, "Further Purification and Characterization of T4 Endonuclease V", *BIOCHIMICIA ET BIOPHYSICA ACTA*, 1976, Vol. 442, pages 197-207. These methods are similar to the Seawell et al. method, except that they substitute cation exchange (carboxymethyl Sephadex) chromatography for anion exchange (DEAE) chromatography, and add additional chromatography steps including either hydroxylapatite or gel filtration and UV DNA cellulose (the Yasuda and Sekiguchi method also differs from the Seawell et al. method in that it does not include a phosphocellulose step). These methods have the same difficulties as the Seawell et al. method with the additional problems of lower yield, less speed and simplicity, and greater cost.

(3) K. M. Higgins and R. S. Lloyd, "Purification of the T4 Endonuclease V", *MUTATION RESEARCH*, 1987, Vol. 183, pages 117-121.

This method uses an *E. coli* strain which harbors a plasmid containing the phage T4 denV structural gene under the control of the phage lambda rightward promoter. The chromatography steps are single-stranded DNA agarose, chromatofocusing and cation exchange (carboxymethyl-Sephadex). The yield is low compared to the present invention, in that 12 liters of bacteria are required for 15 mg pure enzyme. The yield is also limited by the requirement that all proteins bind to the chromatofocusing column in order to elute the desired enzyme. The method is not rapid: each chromatography step is preceded by dialysis and concentration by ultrafiltration; at least two of the steps require on the order of 17.5 hours for elution; and each step is followed both by enzyme activity assays and polyacrylamide gel analysis of each fraction. The method is not simple: the single-stranded DNA agarose chromatography requires pooling of 84% of the collected fraction (520 ml of 700 ml eluent), extensively diluting the loaded protein; experiments in connection with the present invention showed that the chromatofocusing step was not reproducible using DEAE agarose and Servalyte ampholines; ultrafiltration is required in addition to dialysis; and tedious, repetitive activity assays and gel analysis are performed after each step. The method is expensive: large ultrafiltration devices are used and discarded at every step; the single-stranded DNA agarose is exposed to crude bacterial lysates with active nucleases which drastically reduce the useful life of the column; and costly chromatofocusing reagents including Pharmacia PBE 94 gel and polybuffer ampholines must be used.

In addition to the foregoing, two methods have been published for the purification of $O^6$-methylguanine-DNA methyltransferase. See B. Demple, A. Jacobsson, M. Olsson, P. Robbins and T. Lindahl, "Repair of Alkylated DNA in *Escherichia coli*: Physical properties of $O^6$-methylguanine-DNA methyltransferase" in *THE JOURNAL OF BIOLOGICAL CHEMISTRY*, vol. 257, pages 13776-13780, 1982, and Y. Nakabeppu, H. Kondo, S. Kawabata, S. Iwanaga and M. Sekiguchi, "Purification and Structure of the Intact Ada Regulatory Protein of *Escherichia coli* K12 $O^6$-Methylguanine-DNA Methyltransferase" in *THE JOURNAL OF BIOLOGICAL CHEMISTRY*, vol. 260, pages 7281-7288, 1986. The Demple method uses phosphocellulose chromatography before DNA-cellulose and gel filtration, and includes a final phenylagarose chromatography step. The Nakabeppu method uses two rounds of ion-exchange (DEAE-) chromatography followed by phosphocellulose and gel filtration chromatography.

A general review of purification methods for DNA repair enzymes can be found in *DNA REPAIR: A LABORATORY MANUAL OF RESEARCH PROCEDURES*, edited by E. Friedberg and P. C. Hanawalt, published by Marcel Dekker, N.Y. Volume I, part A, of this text contains methods for purifying five enzymes: photolyase, endonuclease V (discussed above), AP endonuclease, uracil-DNA glycosylase and hypoxanthine-DNA glycosylase, in chapters 18-22, respectively. Volume II, chapters 3-5, discuss the Demple method referred to above and methods for purifying 3-methyladenine-DNA glycosylases. Volume III, Section IV, contains methods for purification of photolyase, the uvrABC excision nuclease and the uvrD helicase in chapters 23-25. None of these methods, nor the two methods discussed above for purifying $O^6$-methylguanine-DNA methyltransferase, use the purification procedures of the present invention.

Various approaches have been considered in the field of DNA repair for delivering DNA repair enzymes to mammalian cells. The goal of these efforts has been to discover and characterize the pathways of DNA repair in mammalian cells and their evolution, not to develop commercial methods for augmenting DNA repair. Thus, researchers have not used normal cells, such as skin epidermal keratinocyte cells, as target cells, but rather have concentrated on fibroblasts from patients with xeroderma pigmentosum. Similarly, prior research has focused on non-physiological techniques for introducing DNA repair enzymes into cells which are useful only in the laboratory and which compromise the physiology of the target cells. The published reports regarding this work include:

(1) K. Tanaka, M. Sekiguchi and Y. Okada, "Restoration of ultraviolet-induced unscheduled DNA synthesis of xeroderma pigmentosum cells by the concomitant treatment with bacteriophage T4 endonuclease V and HVJ (Sendai virus)", *PROCEEDINGS OF THE NATIONAL ACADEMY OF SCIENCES* U.S.A., 1975, Vol. 72, pages 4071-4075; and K. Tanaka, H. Hayakawa, M. Sekiguchi and Y. Okada, "Specific action of T4 endonuclease V on damaged DNA in xeroderma pigmentosum cells in vivo", *PROCEEDINGS*

*OF THE NATIONAL ACADEMY OF SCIENCES U.S.A.*, 1977, Vol. 74, pages 2958-2962.

In these two reports, fibroblasts derived from patients with xeroderma pigmentosum were treated with inactivated Sendai virus and endonuclease V after UV irradiation. Proteins on the coat of the Sendai virus rendered the cells permeable to endonuclease V. This treatment enhanced DNA repair replication and increased survival of the treated cells. This method of introducing the enzyme is not practical for commercial application because of the pathogenicity of the Sendai virus. Large external enzyme concentrations are also required. In its discussion section, the Tanaka et al. reference discusses approaches to the study of the evolution of macromolecular (i.e. DNA repair) systems in organisms and mentions liposome methods and erythrocyte ghost/HVJ methods as other methods for introducing macromolecules into cells. Significantly, Tanaka et al. ultimately conclude that the Sendai virus method is the most simple and applicable method in basic research for the introduction of rather small macromolecules of about 20,000 daltons, i.e., the T4 endonuclease V molecule.

(2) G. Ciarrocchi and S. Linn, "A cell-free assay measuring repair DNA synthesis in human fibroblasts", *PROCEEDINGS OF THE NATIONAL ACADEMY OF SCIENCES U.S.A.*, 1978, Vol. 75, pages 1887-1891.

In this report, human normal and xeroderma pigmentosum fibroblasts were disrupted by osmotic shock after UV irradiation, and incubated with endonuclease V. DNA repair synthesis was increased in both types of cells, and repair in xeroderma pigmentosum cells increased to the level of normal cells. This method for introducing enzyme into cells was only employed for in vitro research, as it destroys the integrity of the cell membrane and viability is drastically affected. Large external enzyme concentrations are also required.

(3) D. Yarosh and R. Setlow, "Permeabilization of Ultraviolet-irradiated Chinese hamster cells with polyethylene glycol and introduction of ultraviolet endonuclease from *Micrococcus luteus*", *MOLECULAR AND CELLULAR BIOLOGY*, 1981, Volume 1, pages 237-244.

In this method, hamster cells were treated with polyethylene glycol after UV irradiation and then incubated with a DNA repair enzyme which acts similarly to endonuclease V. The enzyme entered the cells and acted on resident DNA. The method was toxic to target cells, probably because it relied on permeabilization, and vital molecules exited as the enzyme entered. This method also requires large external enzyme concentrations for efficacy.

(4) J. H. J. Hoeijmakers, "Characterization of genes and proteins involved in excision repair of human cells", *JOURNAL OF CELL SCIENCE SUPPL.*, 1987, Vol. 6, pages 111-125.

This reference summarizes a body of research in which proteins were introduced into the nuclei of cells by microinjection. When endonuclease V was injected into the nuclei of xeroderma pigmentosum cells, DNA repair synthesis was increased. This method is applicable only for laboratory research.

(5) K. Valerie, A. P. Green, J. K. de Riel and E. E. Henderson, "Transient and stable complementation of ultraviolet repair in xeroderma pigmentosum cells by the denV gene of bacteriophage T4", *CANCER RESEARCH*, 1987, Vol. 47, pages 2967-2971.

In this method, the denV gene under the control of a mammalian promoter was transfected into xeroderma pigmentosum cells. Clones selected for uptake of the denV gene showed increased incision of UV-DNA, enhanced DNA repair synthesis and increased resistance to ultraviolet irradiation. The transfection process is very inefficient (less than one success per million cells) for normal human cells. These methods fall into the category of gene therapy, and are beyond the scope of the current art for commercial use.

SUMMARY OF THE INVENTION

In view of the foregoing state of the art, it is an object of the present invention to provide improved methods for purifying DNA repair enzymes. In particular, it is an object of the invention to provide methods for purifying DNA repair enzymes which are rapid, simple to use, inexpensive, and which produce a high yield of a homogenous final product.

It is a further object of the invention to provide non-toxic methods and means for administering DNA repair enzymes in active form to living cells in situ. In particular, it is an object of the invention to provide administration methods and means which do not involve significant changes in the permeability properties of the membranes of the living cells. It is also an object of the invention to provide administration method and means which can be used to topically apply DNA repair enzymes to human skin in situ.

In connection with the foregoing objects, it is a further and specific object of the invention to purify the T4 endonuclease V enzyme and to administer this enzyme to human skin cells.

To achieve the foregoing and other objects, the invention in accordance with certain of its aspects provides a method for purifying DNA repair enzymes comprising the steps of:

(a) applying an aqueous solution of the DNA repair enzyme in an impure state (e.g., an extract of cells which have been genetically engineered to produce the DNA repair enzyme) to a molecular sieve (e.g., a gel filtration column) having a mean pore size such that the exclusion limit (measured either by molecular weight or by Stokes' radius) is:

(i) larger than the measured molecular weight or Stokes' radius of the DNA repair enzyme (e.g., in the case of T4 endonuclease V, an exclusion limit larger than about 16,500 daltons or about 18 Angstroms), and (ii) smaller than the estimated molecular weight or Stokes' radius of at least some of the impurities (e.g., an exclusion limit smaller than about 60,000 daltons or about 35 Angstroms);

(b) isocratically eluting the DNA repair enzyme from the molecular sieve with an elution buffer so as to obtain the DNA repair enzyme in one or more selected fractions of the eluate in a state of enhanced purity, the elution buffer being chosen so that complexes can form between the DNA repair enzyme and selected nucleic acids;

(c) contacting the one or more selected fractions of step (b) with one or more selected nucleic acids (e.g., single-stranded DNA) which have been immobilized on a solid support (e.g., CNBr-activated Sepharose) so as to form immobilized nucleic-acid/DNA-repair-enzyme complexes between the DNA repair enzyme and the one or more selected, immobilized nucleic acids;

(d) washing the immobilized complexes (e.g., with the elution buffer) to remove at least some of the remaining impurities; and (e) eluting the DNA repair enzyme from the one or more selected, immobilized nucleic acids with an elution buffer containing a gradient of a material (e.g., NaCl) capable of disassociating the DNA repair enzyme from the one or more selected, immobilized nucleic acids so as to obtain the DNA repair enzyme in one or more selected fractions of the eluate in a state of further enhanced purity.

As demonstrated by the examples presented below, in the preferred embodiments of the invention, the DNA repair enzyme is obtained as a homogeneous protein at the end of step (e).

This purification process takes advantage of two highly specific characteristics of most DNA repair enzymes: their small size and their affinity for nucleic acids, in particular, single-stranded DNA. Proteins are separated by molecular sieve (gel) filtration, excluding the vast majority of proteins larger than DNA repair enzymes, while retarding the elution of DNA repair enzymes. Because the filtration column is eluted isocratically with almost any buffer, the retarded proteins can be loaded directly onto a nucleic acid affinity column without assay, dialysis or concentration. The nucleic acid affinity column is then developed with either non-specific changes (e.g., gradients of salt, pH, detergent, voltage or temperature) or specific changes (e.g., competing ligand), eluting the DNA repair enzyme in a concentrated form. Since the condition required to elute a protein from a nucleic acid affinity column is a unique characteristic of the protein, the peak of pure DNA repair enzyme can be pooled without assay. The process thus meets the goals of commercial protein purification: it produces homogenous, pure enzyme; it has high yield because only the desired proteins are retained on the chromatography columns; it is rapid and can be completed in one day: it is simple and requires no dialysis or activity assays; and it is inexpensive in not consuming disposable reagents in dialysis or assays and in protecting nucleic acid affinity columns from crude cell lysates.

As fully described in the examples set forth below, the purification procedure of the invention has been successfully applied to the purification of the T4 endonuclease V enzyme. In outline, *E. coli* harboring a plasmid with the denV structural gene under the control of the TAC promoter were grown to log phase and denV gene expression was induced by the addition of isopropylthiogalactopyranoside. A cell lysate was prepared, concentrated and dialyzed against the buffer subsequently used in both gel filtration and DNA affinity chromatography. The pore diameter of the gel filtration media was selected to exclude from the gel most contaminating proteins while including the desired T4 endonuclease V protein. The cell lysate was applied to the gel filtration column and eluted isocratically, the excluded proteins being discarded and the retained proteins being collected. The retained proteins were then applied directly to a single-stranded DNA agarose column. The column was washed and then developed with a salt gradient. The eluent was monitored for optical density at 280 nm and the peak of optical density was pooled. This peak comprised the desired denV endonuclease V enzyme which was subsequently shown to have been purified to homogeneity.

In addition to the foregoing purification procedures, the present invention also provides methods and means for administering DNA repair enzymes to living cells. In particular, in accordance with these aspects of the invention, DNA repair enzymes are encapsulated in liposomes to form pharmaceutical preparations suitable for administration to living cells and, in particular, suitable for topical administration to human skin. When delivered to human cells in this form, the DNA repair enzymes will enter the cells, incise damaged DNA, enhance DNA repair synthesis and increase cell survival after exposure to ultraviolet light.

In comparison with prior art methods, the delivery system of the invention has the advantages of requiring high enzyme concentration only within the liposomes and not in the general exterior of the cells, and of delivering the enzyme while preserving the integrity of the target cells. Also, by suitable modifications of the liposome membranes, the liposomes can be made to bind to specific sub-populations of cells, thereby increasing the efficiency and/or specificity of enzyme delivery. As result of these improvements, the invention allows DNA repair enzymes to be used clinically, either before or after exposure to ultraviolet light, to help combat skin cancer caused by UV-damaged DNA in both normal individuals and patients suffering from xeroderma pigmentosum.

As fully described in the examples presented below, the delivery system of the invention has been successfully used to administer endonuclease V to normal human epidermal keratinocytes and fibroblasts and transformed human normal and xeroderma pigmentosum cells. In outline, a lipid mixture was dissolved in organic solvents and dried to a thin film in a glass vessel. Endonuclease V which had been purified in accordance with the methods of the present invention was added to the vessel at high concentration in an aqueous buffer to rehydrate the lipid. The mixture was then agitated by vortexing and sonicated to form liposomes. The spheres were then separated from unincorporated enzyme by centrifugation or gel filtration. The liposomes were then diluted into media and added to the target cells. The addition of the liposomes to the cells resulted in enhanced DNA repair as evidenced by increased UV-specific incision, increased DNA repair replication, and increased UV-survival.

DESCRIPTION OF THE PREFERRED EMBODIMENTS

Figure 3:
FIG. 3 is a photograph of liposomes containing T4 endonuclease V which have been immunofluorescently stained. Liposomes composed of phosphatidylcholine and cholesterol (9:1 molar ratio) and T4 endonuclease V were dried on a glass slide and fixed with ice-cold acetone. The slide was blocked with 1% bovine serum albumin and stained with rabbit anti-T4 endonuclease V IgG antibodies, and goat anti-rabbit antibodies conjugated to alkaline phosphatase. The sites of antibody binding were revealed by incubation with 4-methylumbelliferyl phosphate (4-MUP) which was cleaved by the alkaline phosphatase to a fluorescent dye and visualized by fluorescent microscopy. The bright circles of various sizes are stained liposomes containing T4 endonuclease V.

As discussed above, the present invention relates to 1) a method for purifying DNA repair enzymes through the sequential use of a molecular sieve chromatography column and a nucleic acid affinity column, and 2) the use of liposomes to administer DNA repair enzymes to living cells.

The purification and administration aspects of the invention can be applied to a variety of DNA repair enzymes now known or subsequently developed or discovered. In particular, the invention can be used with phage T4 endonuclease V, $O^6$-methylguanine-DNA methyltransferases, and with the other DNA repair enzymes discussed and listed above.

With regard to the purification aspects of the invention, the first step of the purification process—molecular sieving—serves to separate the DNA repair enzymes from the vast majority of proteins with larger sizes based on relative rates of migration of the DNA repair enzymes and the contaminating proteins through the molecular sieve matrix.

Molecular sieving can be accomplished by many methods, including gel filtration and electrophoresis. In gel filtration proteins flow around and through pores in beads made from dextran, polyacrylamide, agarose, agarose and acrylamide composites, or other materials. The size of the bead pores include or exclude proteins based on size. In electrophoresis, proteins move in an applied electric field through a sizing matrix.

The preferred molecular sieving method for use with the present invention is gel filtration because the enzyme can be easily recovered and because the method is independent of such factors as net protein charge. The pore size of the beads used with this method are selected to maximize separation of DNA repair enzymes from the bulk of other proteins. A general guideline for selecting the gel filtration matrix is that the gel should have an exclusion limit greater than about twice the molecular weight or Stokes' radius of the DNA repair enzyme and less than about 60,000 daltons or 35 Angstroms.

A wide variety of elution buffers may be used to elute the DNA repair enzyme from the gel filtration column. The selected buffer should satisfy the following criteria: 1) the buffer should not denature or inactivate the DNA repair enzyme, 2) the buffer should not permit ionic adsorption of the DNA repair enzyme to the gel filtration media, and 3) the buffer should be compatible with loading of the eluate onto the nucleic acid affinity column, that is, the elution buffer should be chosen so that complexes will form between the DNA repair enzyme and the immobilized nucleic acids of the affinity column.

The second step of the purification process—nucleic acid binding—separates the DNA repair enzymes from the remaining protein impurities by the ability of DNA repair enzymes to reversibly bind to nucleic acids. Separation by nucleic acid binding can be accomplished by various methods, including nucleic acid affinity chromatography. In this method, nucleic acids are immobilized on an inert matrix, such as agarose, polyacrylamide beads, cellulose or other media. Depending on the DNA repair enzyme which is being purified, the immobilized nucleic acids may be double- or single-stranded DNA, double- or single-stranded RNA, or other types, lengths, structures or combination of nucleic acids, such as tRNA, Z-DNA, supercoiled DNA, ultraviolet-irradiated DNA or DNA modified by other agents. Single-stranded DNA is in general preferred.

The nucleic acids may be attached to the solid phase matrix by a variety of methods, including covalent attachment of the nucleic acid through primary amines or by adsorbing the nucleic acids to a matrix such as cellulose, which releases nucleic acids slowly. The preferred immobilization method is to use cyanogen-bromide activated Sepharose and to bind the nucleic acids to the activated Sepharose covalently.

The DNA repair enzymes are applied to the nucleic acids in a solution which should satisfy the following criteria: 1) the solution should permit reversible binding of the DNA repair enzyme to the nucleic acids, 2) the solution should reduce non-specific binding of contaminating proteins to the nucleic acids, and 3) the solution should not cause damage to the nucleic acids. In general, a neutral buffered solution with physiological saline and 1 mM EDTA will satisfy these criteria. As discussed above, in accordance with the invention, the elution fractions from the molecular sieve column are applied directly to the nucleic acid affinity column. Accordingly, the elution buffer used with the molecular sieve column should be chosen to satisfy the foregoing criteria.

The bound DNA repair enzymes are eluted from the nucleic acid affinity column with a gradient which removes the enzyme from the nucleic acid at a characteristic condition and concentrates the enzyme by the focusing effect of the gradient. The elution system, however, should not denature the enzyme or introduce contaminants into the final product. A gradient of NaCl up to 1.0M will in general be sufficient to reverse binding of most DNA repair enzymes to nucleic acids. In appropriate cases, the gradient may be one of another salt, increasing or decreasing pH, temperature, voltage or detergent, or, if desired, a competing ligand may be introduced to replace the nucleic acid binding.

With regard to the administration aspects of the invention, the liposomes which are used to administer the DNA repair enzymes can be of various types and can have various compositions. The primary restrictions are that the liposomes should not be toxic to the living cells and that they should deliver their contents into the interior of the cells being treated.

The liposomes may be of various sizes and may have either one or several membrane layers separating the internal and external compartments. The most important elements in liposome structure are that a sufficient amount of enzyme be sequestered so that only one or a few liposomes are required to enter each cell for delivery of the DNA repair enzyme, and that the liposome be resistant to disruption. Liposome structures include small unilamellar vesicles (SUVs, less than 250 angstroms in diameter), large unilamellar vesicles (LUVs, greater than 500 angstroms in diameter), and multilamellar vesicles (MLs). In the examples presented below, SUVs are used to administer DNA repair enzymes. SUVs can be isolated from other liposomes and unincorporated enzyme by molecular sieve chromatography, which is precise but time consuming and dilutes the liposomes, or differential centrifugation, which is rapid but produces a wider range of liposome sizes.

The liposomes may be made from natural and synthetic phospholipids, glycolipids, and other lipids and lipid congeners; cholesterol, cholesterol derivatives and other cholesterol congeners; charged species which impart a net charge to the membrane; reactive species which can react after liposome formation to link additional molecules to the liposome membrane; and other lipid soluble compounds which have chemical or biological activity.

Liposome membranes undergo a phase transition from crystalline to liquid at a temperature (Tc) characteristic of the phospholipid composition. When the phospholipid is heated above Tc and then cooled, the membrane retains water in its amphiphilic lattice and has the characteristics of a gel. In order to achieve the liquid or gel state, the phospholipid composition must be such that the Tc is lower than the temperature which inactivates the entrapped enzyme. Cholesterol in the phospholipid mix effectively reduces the Tc by broadening the range at which phase transition occurs. In view of these requirements, a suitable mixture for preparing the liposomes of the present invention comprises phosphotidyl choline (or a derivative thereof with a Tc of less than 42° C.), dicetyl phosphate (or a negatively charged species at neutrality), and cholesterol (or a cholesterol derivative) at a molar ratio of 7:2:1.

The liposomes of the present invention are prepared by combining a phospholipid component with an aqueous component containing the DNA repair enzyme under conditions which will result in vesicle formation. The phospholipid concentration must be sufficient to form lamellar structures, and the aqueous component must be compatible with biological stability of the enzyme. Methods for combining the phospholipid and aqueous components so that vesicles will form include: drying the phospholipids onto glass and then dispersing them in the aqueous component; injecting phospholipids dissolved in a vaporizing or non-vaporizing organic solvent into the aqueous component which has previously been heated; and dissolving phospholipids in the aqueous phase with detergents and then removing the detergent by dialysis. The concentration of the DNA repair enzyme in the aqueous component can be increased by lyophilizing the enzyme onto dried phospholipids and then rehydrating the mixture with a reduced volume of aqueous buffer. SUVs can be produced from the foregoing mixtures either by sonication or by dispersing the mixture through either small bore tubing or through the small orifice of a French Press.

In the examples presented below, SUVs were prepared by drying phospholipids onto glass, rehydrating them in aqueous buffer containing the DNA repair enzyme with shaking at 37° C., sonicating the resulting mixture, and isolating the SUVs containing the DNA repair enzyme by molecular sieve chromatography and concentrating the SUVs by centrifugation. FIG. 3 illustrates the success of this technique for incorporating DNA repair enzymes into liposomes.

DNA repair enzymes incorporated into liposomes can be administered to living cells internally or topically. Internal administration to animals or humans requires that the liposomes be pyrogen-free and sterile. To eliminated pyrogens, pyrogen-free raw materials, including all chemicals, enzymes, and water, are used to form the liposomes. Sterilization can be performed by filtration of the liposomes through 0.2 micron filters. For injection, the liposomes are suspended in a sterile, pyrogen-free buffer at a physiologically effective concentration. Topical administration also requires that the liposome preparation be pyrogen-free, and sterility is desirable. In this case, a physiologically effective concentration of liposomes can be suspended in a buffered polymeric glycol gel for even application to the skin. In general, the gel should not include non-ionic detergents which can disrupt liposome membranes. Other vehicles can also be used to topically administer the liposomes. The concentration of the enzyme in the final preparation can vary over a wide range, a typical concentration being on the order of 50 ug/ml.

General discussions of liposomes and liposome technology can be found in an article entitled "Liposomes" by Marc J. Ostro, published in *SCIENTIFIC AMERICAN*, Jan. 1987, volume 256, pages 102-111, and in a three volume work entitled *LIPOSOME TECHNOLOGY*, edited by G. Gregoriadis, 1984, published by CRC Press, Boca Raton, Fla. The pertinent portions of each of these references are incorporated herein by reference.

Without intending to limit it in any manner, the present invention will be more fully described by the following examples.

EXAMPLE 1

Purification of Endonuclease V (1) Enzyme purification.
(A) Cell growth and induction. The *E. coli* strain SR1268 harboring the plasmid pTACdenV is described by J. Chenevert, L. Naumovski, R. A. Schultz and E. C. Friedberg, *MOLECULAR AND GENERAL GENETICS*, 1986, Vol. 203, pages 163-171. A sample of this strain was obtained from Dr. Errol Friedberg, Department of Pathology, Stanford University, School of Medicine, Stanford, Calif. 94305. A culture of the bacteria was prepared in 200 ml LB+amp (10 g/l tryptone, 5 g/l yeast extract, 10 g/l NaCl, 125 ug/ml ampicillin, pH 7.5) and incubated overnight at 37° C. The culture was diluted to 2 liters in LB+amp and incubated at 37° C. until the optical density at 600 nm was 0.3. Isopropyl-beta-D-thiogalactopyranoside was added to 1 mM and the incubation continued for 60 min.

(B) Cell lysis and protein precipitation. The cells were collected by centrifugation at 12,785×g for 15 min at 4° C., and were resuspended in 200 ml of TES (50 mM Tris, pH 8.0, 50 mM $Na_2$EDTA, 15% sucrose). 0.2 g of lysozyme was added and the mixture was incubated at 25° C., for 30 min. 160 ml ice cold distilled water and 40 ml 10% streptomycin sulfate were then added, and stirred at 4° C. for 30 min. The lysate was centrifuged at 15,188×g for 15 min. and the supernatant was collected. 83.2 g of ammonium sulfate was slowly added with stirring at 4° C., and stirring was continued for 30 min. The mixture was centrifuged at 15,188×g for 15 min, and the supernatant was collected. 79.6 g ammonium sulfate was added and stirred at 4° C. for 30 min. The mixture was centrifuged at 15,188×g for 15 min, and the precipitate was resuspended in Buffer A (50 mM Tris, pH 8, 50 mM NaCl, 1 mM EDTA, 1 mM dithiothreitol, 0.1 mM phenylmethylsulfonyl fluoride) and dialyzed against 1.0 l Buffer A overnight at 4° C.

(C) Gel filtration. The dialyzed proteins were loaded on a standard column (2.5 cm d. ×30 cm) of AcA54 gel filtration media (LKB) at a flow rate of 50 ml/hr. The proteins were eluted isocratically with Buffer A, and fractions of 5 ml were monitored for optical density at 280 nm. The second large peak of protein, which elutes at approximately R(f)=1.67, was pooled.

(D) Single-stranded DNA chromatography. Single-stranded DNA Sepharose was prepared by boiling calf thymus DNA and covalently attaching it to CNBr-activated Sepharose (Pharmacia) according to the manufacturer's instructions. This was packed in a Superflo 50 radial flow column (Sepragen). The second peak of protein from gel filtration was loaded directly onto the single-stranded DNA column at a flow rate of 400 ml/hr and washed with 250 ml of Buffer A. At the same flow rate the column was developed with a 200 ml linear gradient of 50 mM to 1.0 M NaCl in Buffer A. Fractions of 5 ml were monitored for optical density at 280 nm. The peak of protein which elutes at about midway in gradient development was pooled. As demonstrated below, this peak was pure endonuclease V.

(E) Storage. Herring sperm DNA was added to the enzyme to a concentration of 20 ug/ml and the resulting mixture was dialyzed overnight at 4° C. against a buffer of 50 mM Tris, pH 8.0, 100 mM NaCl, 10 mM EDTA, 1 mM dithiothreitol, 0.1 mM phenylmethylsulfonyl fluoride. Polyethylene glycol was added to the mixture at a concentration of 3% and the final solution was stored at 4° C. until used.

(2) Assay for endonuclease V activity.

The assay used to measure endonuclease V activity measured the relaxation by the enzyme of supercoiled plasmid DNA produced by single-stranded breaks introduced in UV-irradiated DNA. A unit of enzyme activity is defined as the amount of enzyme which will produce on the average one break per molecule in 1 ng of pBR322 plasmid irradiated with 40 $J/m^2$ of 254 nm UV in a 10 min. incubation at 37° C.

(A) Substrate. Plasmid pBR322 was irradiated with 40 $J/m^2$ of 254 nm UV and mixed with unirradiated plasmid pSV2neo. Because the pBR322 plasmid is smaller than the pSV2neo plasmid, both its supercoiled and relaxed forms migrate faster in neutral agarose gels than the corresponding forms of pSV2neo. However, the supercoiled form of pSV2neo migrates faster than the relaxed form of pBR322. The substrate for the assay is the UV-irradiated pBR322 DNA and the pSV2neo DNA serves as a control for non-specific nuclease activity. The substrate DNA was prepared at 20 ug/ml of each plasmid in Endo V Buffer (50 mM $NaH_2PO_4$, 100 mM NaCl, 10 mM EDTA, 1 mM DTT, 0.1 ug/ml bovine serum albumin, pH 6.5).

(B) Reaction. 25 ul of substrate DNA was mixed with 25 ul of enzyme preparation from step 1(E) above, diluted in Endo V Buffer, and incubated at 37° C. for 10 min. The reaction was stopped by addition of 5 ul 10×Gel Loading Buffer (0.25% bromophenol blue, 30% Ficoll).

(C) Agarose gel electrophoresis. A 0.8% agarose gel was prepared in TAE buffer (40 mM Tris, pH 8.4, 5 mM sodium acetate, 1 mM EDTA). 10 ul of each reaction was loaded and electrophoresed at 7 V/cm. When the dye had migrated 2/3 of the gel length, the gel was soaked in ethidium bromide (1 ug/ml), destained in 1 mM $MgSO_4$, and viewed by transillumination with 360 nm UV. The gel was photographed using a red Wrattan filter and Polaroid positive/negative film Type 665. The negative was washed in distilled water.

(D) Film analysis. For quantitation of endonuclease activity, the negative was scanned by a densitometer and the analog voltage readings were stored in digital form in a computer. Labtech Chrom software (Laboratory Technologies Corporation, Wilmington, Mass.) was used to integrate the area of each band detected by densitometry. The average number of breaks in each plasmid was calculated from the natural log of the fraction of supercoiled molecules. The average number of UV-specific breaks was calculated from the difference in average breaks between pBR322 and pSV2neo DNA, corrected for the difference in untreated samples.

(3) Results.

Figure 1:
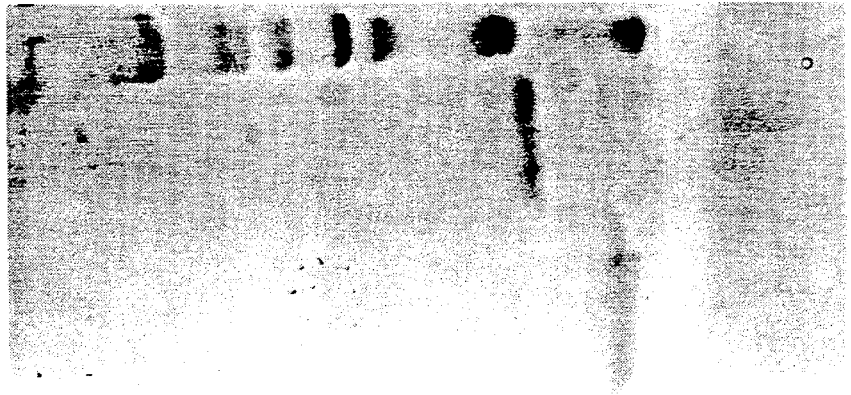
FIG. 1 shows the results of polyacrylamide gel electrophoresis of T4 endonuclease V and $O^6$-methylguanine-DNA methyltransferase purified by the present invention. Twenty-five ug of purified T4 endonuclease V (left lane) and 25 ug of purified methyltransferase (center lane) were denatured with SDS, loaded on a 15% discontinuous polyacrylamide gel and electrophoresed with molecular weight markers (right lane). The size of the molecular weight markers from the top were: 67,000; 45,000; 36,000; 29,000; 24,000; 20,100; and 14,200. The proteins in the gel were stained with Coomassie blue. The gel shows that each protein was homogenous and pure and of the appropriate size (16,500 for T4 endonuclease V and 19,000 for methyltransferase).

Typical results from the purification process of the invention were as follows: Two liters of bacterial culture were prepared and lysed. After the precipitation of nucleic acids by streptomycin sulfate, 660 mg of protein remained. 525 mg of protein were recovered from ammonium sulfate precipitation and loaded onto the gel filtration column, and 15 mg of pure endonuclease V were recovered after the DNA affinity column at a concentration of 0.2 mg/ml. The enzyme activity was 10,000 units per ug protein. The preparation produced a single band on polyacrylamide gel electrophoresis (see FIG. 1) and only a single band appeared on Western blots of protein probed with rabbit antiserum to endonuclease V. The enzyme was stable for at least four months at 4° C., at least 5 days at 37° C., and had a half life at 42° C. of greater than 30 min.

EXAMPLE 2

Purification of O$^6$-Methylguanine-DNA Methyltransferase

O$^6$-methylguanine-DNA methyltransferase is a DNA repair enzyme which removes alkyl groups from DNA and transfers them to itself in a suicide reaction. The properties of this enzyme have been summarized by Daniel Yarosh, in a review entitled "The role of O$^6$-methylguanine-DNA methyltransferase in cell survival, mutagenesis and carcinogenesis", published in *MUTATION RESEARCH*, volume 145, pages 1-16, 1985.

(1) Enzyme purification.

(A) Cell growth and induction. *E. coli* strain N445 harboring the plasmid pSM31 was grown to stationary phase in LB+amp, as described above in Example 1. The plasmid pSM31 contains the entire ada gene with its own promoter, and codes for the *E. coli* O$^6$-methylguanine-DNA methyltransferase. A sample of the N445 strain was obtained from Dr. Sankar Mitra, Biology Department, Oak Ridge National Laboratory, Oak Ridge, Tenn. 37831. The production of the transferase by these cells was induced by adding N-methyl-N'-nitro-N-nitrosoguanidine to a concentration of 0.5 ug/ml, and incubating the culture at 37° C. for 90 min.

(B) Cell lysis and protein precipitation. The cells were collected and lysed by the same methods as described in Example 1. Nucleic acids were precipitated by streptomycin sulfate as described in Example 1. Ammonium sulfate was added at 112 g per 200 ml supernatant, and stirred at 4° C. for 60 min. The precipitated proteins were collected by centrifugation at 15,188×g for 30 min, resuspended in 5 ml of Buffer A, and dialyzed overnight against 1.0 l Buffer A at 4° C.

(C) Gel filtration and single-stranded DNA chromatography. Chromatography of the cell lysate was performed as described for endonuclease V. The transferase eluted from the AcA54 gel as a shoulder on the first large optical density peak, and from single-stranded DNA after about one-third of the gradient. As demonstrated below, the pooled peak was pure O$^6$-methylguanine-DNA methyltransferase.

(2) Assay for O$^6$-methylguanine-DNA methyltransferase activity.

The assay used to measure the activity of the O$^6$-methylguanine-DNA methyltransferase enzyme measured the transfer of radiolabeled methyl groups from DNA to protein, and has been described by B. Myrnes, K. Nordstrand, K. Giercksky, C. Sjunneskog and H. Krokan in a paper entitled "A simplified assay for O$^6$-methylguanine-DNA methyl transferase and its application to human neoplastic and non-neoplastic tissues," published in CARCINOGENESIS, 1984, volume 5, pages 1061-1064.

(A) Substrate. The substrate for the assay was DNA alkylated with a simple methylating agent and then enriched for O$^6$-methylguanine by depurinating other alkylated purines. Calf thymus DNA at 5 mg/ml was reacted with methylnitrosourea containing tritium in the methyl moiety at 1 mCi per ml of a 0.2M sodium cacodylate buffer, pH 7, 5 mM EDTA, at 37° C. for 4 hr. The DNA was precipitated by ethanol, washed with ethanol, and resuspended at 2.5 mg/ml in 0.1 M NaCl, 10 mM sodium citrate, 10 mM potassium dihydrogen phosphate, pH 7.4. The DNA was heated at 80° C. for 16 hrs., ethanol precipitated, washed and resuspended in 10 mM Tris, pH 7, 1 mM EDTA. This substrate contained more than half of all labeled adducts as O$^6$-methylguanine.

(B) Reaction. 0.33 pmol of O$^6$-methylguanine in DNA was mixed with the enzyme preparation in transferase buffer of 70 mM Hepes, pH 7.1, 1 mM EDTA, and incubated at 37° C. for 30 min to allow transfer of labeled adducts from DNA to protein. The mixture was brought to 5% trichloroacetic acid and heated at 80° C. for 30 min to precipitate proteins and solubilize unreacted O$^6$-methylguanine. The precipitated proteins were separated from solubilized bases by filtering through glass fiber filters. The filters were washed with ethanol and the trapped radioactivity measured by scintillation counting. The amount of transferase was calculated from the trapped radioactivity and the known specific activity of the labeled methylated bases.

(3) Results

Typical results from this purification were as follows: After precipitation of nucleic acids from 2.0 l of cell extract, 218 mg of protein were loaded on the gel filtration column, 77 mg of protein were collected and loaded on the single-stranded DNA column, and 14 mg of pure O$^6$-methylguanine-DNA methyltransferase were recovered. Enzyme activity was 3,000 pmol methyl groups transferred per mg protein. The protein showed a single band (see FIG. 1) on polyacrylamide gels and in Western blots using rabbit antiserum to the transferase protein.

EXAMPLE 3

Encapsulation of denV Endonuclease V in PC/DCP and PC/SA Liposomes (1) Preparation of liposomes.

As discussed above, liposomes may be prepared by many methods using many lipid and non-lipid mixtures over a broad range of concentrations. The following methods were used in this example. 22 mg of egg yolk phosphatidylcholine and either 13.5 mg of dicetyl phosphate or 7.3 mg of stearylamine were dissolved in 5 ml of chloroform. Two mls of this mixture were dried to a film in a 25 ml round bottom flask by an air stream in a water bath at 37° C. The film was further dried by vacuum for 60 min. Two mls of denV endonuclease V at 0.2 mg/ml prepared as described in Example 1 were added, and the mixture vortexed to dissolve the lipid in the aqueous solution. The flask was placed in a sonication bath for 60 min. In the case of phosphatidylcholine/dicetyl phosphate liposomes, the solution was then centrifuged at 12,000×g for 5 min, and the supernatant drawn off and discarded. The pellet of liposomes was resuspended in phosphate buffered saline (PBS) and washed again by centrifugation. The pellet of liposomes was finally resuspended in 1 ml of PBS. In the case of phosphatidylcholine/stearylamine liposomes, the solution was eluted through a 1.5×30 cm column of AcA54 gel filtration media, and 2 ml fractions were collected. The liposomes eluted in fractions 10-13, and these fractions were pooled. Liposome concentration was measured by diluting the suspended liposomes 1:100 and measuring the optical density at 600 nm.

(2) Assay of liposome encapsulation.

(A) Encapsulation efficiency. A radioactive tracer molecule was included in the aqueous protein solution, and the percentage of radioactivity found in the liposome fraction was compared to the radioactivity found in the remaining fraction.

Figure 2:
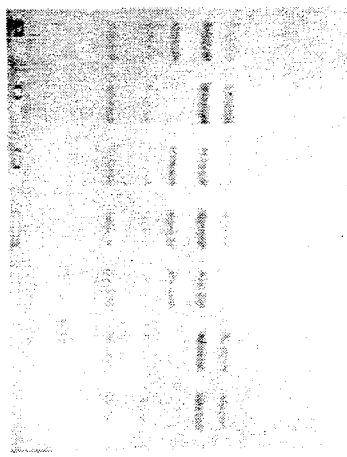
FIG. 2 shows the enzyme activity of T4 endonuclease V encapsulated in liposomes. Liposomes were prepared from phosphatidylcholine/dicetyl phosphate (PC/DCP), phosphatidylethanolamine/dicetyl phosphate (PE/DCP), and phosphatidylglycerol/dicetyl phosphate (PG/DCP) in 7:3 molar ratios in the manner described in the examples below. The liposomes were added to duplicate mixtures of UV and unirradiated plasmids, the second mixture containing 1% Triton X-100 to dissolve the liposomes. After incubation the mixtures were electrophoresed in 0.8% agarose to separate the plasmid forms. Lane 1 contains the plasmid mixture untreated with liposomes. The lowest band is UV-supercoiled plasmid and the next lowest band is unirradiated-supercoiled plasmid. PC/DCP liposomes were added to the mixtures in lanes 2 and 3, of which lane 3 contains Triton X-100. Undissolved liposomes in lane 2 had no effect on the UV-supercoiled plasmid while dissolved liposomes in lane 3 incised the UV-supercoiled plasmid and caused it to migrate in the relaxed form in the third band from the bottom, while migration of the unirradiated supercoiled plasmid was unaffected. PE/DCP liposomes were added to the mixtures in lanes 4 and 5, and PG/DCP liposomes were added to the mixtures in lanes 6 and 7. Triton X-100 was present only in lanes 5 and 7. In each case addition of Triton X-100 revealed UV-specific incising activity of the endonuclease V trapped inside the liposomes.

(B) Endonuclease V activity. The endonuclease V activity assay described in Example 1 was used to measure active enzyme in the liposomes. The liposome preparation was added to duplicate assays, one of which contained 1% Triton X-100 to dissolve the liposomes. Comparison of the activity between intact and dissolved liposomes served as a measure the amount of active enzyme entrapped in liposomes. FIG. 2 illustrates the type of results achieved with this assay protocol.

(3) Results.

Typical results from this method of liposome preparation were as follows: Liposomes were prepared with phosphatidylcholine and stearylamine. Using [H-3]-thymidine as a tracer and separation of liposomes from unincorporated tracer by gel filtration, 42,400 cpm were recovered in the liposome fraction and 10,939,600 cpm were recovered from the remaining fraction, for an encapsulation efficiency of 0.39%. No endonuclease V activity was detected in liposomes without Triton X-100, while dissolved liposomes contained 23,000 units in 1 ml, or 0.59% of the initial activity of 4,000,000 units of endonuclease V.

EXAMPLE 4

Encapsulation of denV Endonuclease V in PC/DCP/Chol and PC/SA/Chol Liposomes (1) Preparation of liposomes.

Liposomes were prepared from phosphatidyl choline, dicetyl phosphate and cholesterol, or from phosphatidyl choline, stearylamine and cholesterol, each in a 7:2:1 molar ratio, in the manner described in Example 3 using the centrifugation technique of example 3 to isolate liposomes.

(2) Assay of liposome encapsulation.

(A) Enzyme concentration. Concentration of the enzyme entrapped in liposomes was measured by enzyme-linked immunosorbent assay (ELISA). Liposomes were diluted to an optical density at 600 nm of 1.0 in 0.1 ml PBS and 25 mM octyl-beta-D-galactopyranoside to dissolve the liposomes. Fifty ul was then diluted in duplicate into 0.2 ml coating buffer (50 mM sodium bicarbonate, pH 9.6, 0.1 mg/ml thimersol) and serially diluted 1:1 down columns of wells in a 96-well microtiter plate. Standards of purified endonuclease V at 5 ug/ml in PBS/octylgalactopyranoside were identically prepared. After overnight incubation at 4° C., the wells were washed with 50 mM Tris, pH 8, 150 mM NaCl (TBS)+0.1% non-idet NP 40 detergent (TBS/NonI), and blocked with 0.2% bovine serum albumin in coating buffer for 2 hours at 25° C. The wells were washed and primary antiserum of rabbit anti-endonuclease V IgG antibodies (5 ug/ml) were added for 2 hours at 25° C. The wells were washed and secondary anti-serum of goat anti-rabbit IgG antibodies conjugated to alkaline phosphatase were added for 30 minutes at 25° C. The wells were washed and o-nitrophenyl phosphate (1 mg/ml) was added. After 30 min. incubation, the optical densities of the wells were measured at 405 nm. The concentration of enzyme in the liposome preparation was calculated from a standard curve of optical density versus enzyme concentration for the endonuclease V standards.

(B) Endonuclease V activity. Endonuclease V activity was determined in the same manner as in Example 3.

(3) Results.

The results of these experiments are shown in Table I. As shown therein, the PC/DCP/Chol liposomes and the PC/SA/Chol liposomes incorporated similar amounts of enzyme in terms of ug/ml. In terms of enzyme activity, however, the PC/SA/Chol liposomes exhibited over four times the activity of the PC/DCP/Chol liposomes.

EXAMPLE 5

Enhancement of Human DNA Repair by Liposomes Containing Endonuclease V (1) Growth and irradiation of human cells in culture.

Human cells were grown using standard tissue culture methods and were used for measuring the enhancement of DNA repair by liposomes containing endonuclease V. The human cells used were: secondary culture of normal human epidermal keratinocytes, normal human fibroblast line WI-38, and SV-40 transformed fibroblast line XP12BE from a patient with xeroderma pigmentosum. All cells were incubated at 37° C. in a humidified 5% CO2 atmosphere attached to plastic dishes. The normal human epidermal keratinocytes were purchased from and cultured according to the directions of Clonetics Corporation, San Diego, Calif., in Keratinocyte Growth Media, which is a modified MDCB-151 media supplemented with bovine pituitary extract. The remaining cells were cultured in Dulbecco's minimal essential media with 10% newborn calf serum, supplemented with antibiotics and vitamins. All cells were grown to near confluence and then subcultured at a 1:4 ratio. For irradiation, the cells were drained of all media, and exposed to a germicidal UV lamp without the dish lid. The lamp output was predominately at 254 nm and the fluence rate was measured by a UVX digital radiometer from Ultra-violet Products, Inc., San Gabriel, Calif., equipped with the UVX-25 probe for 254 nm light. The fluence rate was either 1 J/m$^2$/sec or 2.5 J/m$^2$/sec in all experiments.

(2) Assays for enhanced DNA repair.

(A) Alkaline agarose gel assay for liposome-mediated incision of UV-irradiated DNA. The theoretical basis and practical application of the alkaline agarose gel assay for single-stranded breaks is described in a paper authored by Steven E. Freeman, Anthony D. Blackett, Denise C. Monteleone, Richard B. Setlow, Betsy M. Sutherland and John C. Sutherland entitled "Quantitation of Radiation-, Chemical-, or Enzyme-Induced Single Stranded Breaks in Nonradioactive DNA by Alkaline Gel Electrophoresis: Application to Pyrimidine Dimers", published in *ANALYTICAL BIOCHEMISTRY*, volume 158, pages 119–129, 1986. Human cells were irradiated with 100 J/m$^2$ of 254 nm UV, and then media containing liposomes was incubated with the cells for 2 hrs. The media was removed, the cells were scraped from the dish into PBS, and the DNA purified. An aliquot of DNA was electrophoresed at 3 V/cm in a 0.4% agarose gel and stained with 1 ug/ml ethidium bromide. The gel was photographed and the image of the gel lanes on the developed film negative was scanned by a densitometer. The output of the densitometer was converted from analog voltages to digital values and stored in a computer file. DNA molecular weight markers were included in the gel and also scanned. The number average molecular weight of the DNA in each lane was calculated as described by Freeman et al. by calibrating mobility in the gel with the molecular weight markers. Liposome-mediated incision resulted in smaller number average molecular weight DNA than DNA extracted from irradiated cells not treated with liposomes or unirradiated DNA treated with liposomes.

(B) DNA repair replication. Repair of DNA includes resynthesis of damaged DNA excised during repair. Incorporation of radioactive DNA bases during this repair synthesis results in radioactive high molecular weight DNA in cells undergoing repair. The use of this measure of DNA repair synthesis is reviewed in the 1974 *ANNALS OF INTERNAL MEDICINE* paper on xeroderma pigmentosum by J. Robbins et al., referred to above. In the standard method for measuring repair synthesis, human cells were incubated with 0.01 uCi/ml [C-14] thymidine to uniformly label their DNA and then incubated with 10 mM hydroxyurea for 60 min. to suppress normal DNA synthesis. The cells were then irradiated with 100 J/m$^2$ 254 nm UV, and incubated with 10 mM hydroxyurea, liposomes containing endonuclease V and [H-3]-thymidine at 5 uCi/ml for 4 hrs, during which time repair synthesis occurred. The media was removed, and the cells were scraped into PBS, collected on glass fiber filters, then lysed and washed with 5% trichloroacetic acid and ethanol. Unincorporated [C-14]- and [H-3]-thymidine and small molecular weight DNA were washed from the filters, but high molecular weight DNA was precipitated and remained. The filters were dried and the radioactivity measured by scintillation counting. The ratio of [H-3]- to [C-14]-thymidine incorporated into DNA was used as a measure of the amount of repair DNA synthesis per unit DNA. Repair synthesis was normalized to 100% for irradiated samples not treated with liposomes.

(C) Cell survival. Survival of cells following UV irradiation was measured by metabolism of a tetrazolium salt as described by Tim Mosmann in a paper entitled "Rapid Colorimetric Assay for Cellular Growth and Survival: Application to Proliferation and Cytotoxicity Assay", published in the *JOURNAL OF IMMUNOLOGICAL METHODS*, volume 65, pages 55-63, 1983. Living cells metabolize the tetrazolium salt MTT (3-(4,5-dimethyl-thiazol-2-yl)-2,5-diphenyl tetrazolium bromide), which is yellow, to MTT-formazan, which is blue. The formazan can be measured by a multiwell scanning spectrophotometer at 540 nm (such as an ELISA plate reader), and over a range of cell densities a linear relationship exists between formazan formation and cell number. In the experiments measuring cell survival after UV, human cells were seeded at 1,000 cells per well in a 96-well microtiter plate. After overnight incubation, the media was removed and the cells were irradiated with 254 nm UV at a fluence rate of 2.5 J/m$^2$/sec for various doses of UV. Media and liposomes containing endonuclease V were added and the cells were incubated for 5 days. Fresh media containing 1 mg/ml MTT was added and the cells incubated for 4 hours. The media was carefully removed leaving the precipitated MTT formazan on the bottom of the wells, which was solubilized by adding 50 ul per well of dimethyl sulfoxide and incubating at 37° C. for 30 min. The plates were scanned by an ELISA plate reader at 540 nm, and the optical densities of the UV irradiated wells were compared to those of unirradiated wells to determine cell survival.

(3) Results.

(A) Incision of UV-irradiated DNA. A typical result of liposome-mediated incision of UV-irradiated DNA was as follows: liposomes containing endonuclease V were prepared from a lipid mixture of dipalmitoyl-L-alpha-phosphatidyl choline, phosphatidyl choline and cholesterol (DPPC/PC/Chol; 7:2:1 molar ratio) at 20 mM in an aqueous solution containing 0.2 mg/ml endonuclease V. The liposome suspension had an optical density of 0.33 at 600 nm. Confluent WI38 human fibroblast cells were irradiated with 100 J/m$^2$ of UV and were treated with liposomes diluted 100-fold into saline solution for 2 hrs. at 37° C. The DNA was extracted and single-stranded breaks were measured by alkaline gel electrophoresis. As an additional control, extracted DNA was treated with purified endonuclease V to break the DNA at all sites of pyrimidine dimers, and this DNA was also electrophoresed. The gel was photographed, the negative scanned, and the number average molecular weight and the breaks per million bases in DNA were calculated.

The results of these experiments are shown in Table 2. As shown therein, the UV treatment introduced (344.0-62.0)=282 pyrimidine dimer sites per million bases in DNA, of which the treatment with liposomes was able to incise (80.8-62.0)=18.8 sites per million bases, or 6.7% of all sites. This frequency of incision approaches the practical limit of 10–40% achieved with mechanically disrupted WI38 cells and unencapsulated endonuclease V as reviewed in the paper by Yarosh and Setlow, in *MOLECULAR AND CELLULAR BIOLOGY*, 1981, referred to above.

(B) Repair replication. Typical results from experiments on liposome-mediated repair replication were as follows: liposomes were prepared from phosphatidyl choline and dicetyl phosphate (PC/DCP; 7:3 molar ratio) at 20 mM in an aqueous solution of 0.2 mg/ml endonuclease V, and had an optical density of 25.8 at 600 nm. Xeroderma pigmentosum cell line XP12BE and normal human epidermal keratinocytes were equally divided and grown to near confluence in 60 mm dishes, irradiated with 100 J/m$^2$ of 254 nm UV, and treated with various concentrations of liposomes ("OD Liposome" in Table 3). The cells were pulse-labeled with [H-3]-thymidine for 4 hours, and the amount of repair replication was determined by scintillation counting, and expressed as a percentage of control values without liposome treatment. The results of these experiments are shown in Table 3.

The data in this table demonstrate that for UV-irradiated XP12BE cells, incubation with liposomes nearly doubled the amount of DNA repair replication compared to irradiated cells incubated without liposomes. Liposome treatment had little or no effect on XP12BE cells in the absence of UV irradiation. Treatment of UV-irradiated normal human epidermal keratinocytes with liposomes increased the amount of DNA repair replication by 25%. The much larger effect in xeroderma pigmentosum cells than in normal human cells reflects the fact that in xeroderma pigmentosum cells liposome treatment restores a DNA repair process blocked by a biochemical defect, while in normal human cells liposome treatment augments an already active process.

(C) Cell survival after UV irradiation. Typical results of two separate cell survival experiments using the colorimetric assay were as follows: xeroderma pigmentosum XP12BE cells were seeded in wells of 96-well plates at 1,000 cells per well and incubated overnight. The media was removed and the cells irradiated for various doses of UV. Media was added to the wells along with liposomes containing endonuclease V. DPPC/PC/Chol and PC/DCP liposomes were used at optical densities at 600 nm in the media of 0.14 and 0.26, respectively. After 5 days incubation, fresh media with MTT was added, and the plates were scanned after 4 hours incubation. The surviving fraction at each dose was calculated by comparing the optical density of irradiated cells with the optical density of unirradiated cells with the same liposome treatment. The slope of the survival curve and the correlation coefficient of the slope were calculated by linear regression analysis of the log of the surviving fraction plotted against UV dose. The results of these experiments are shown in Table 4.

The theoretical basis for analysis of survival curves is presented by Walter Harm in his book *BIOLOGICAL EFFECTS OF ULTRAVIOLET RADIATION*, Cambridge University Press, Cambridge, 1980. As discussed in chapter 4 entitled "Inactivation of cells and viruses" the fluence reduction factor is the ratio of the slope of untreated cells to the slope of treated cells. It represents the constant factor by which the biological effect of UV irradiation has been attenuated, in this case the reduction in lethality produced by liposome treatment. The fluence reduction factors shown in Table 4 using liposomes approach the theoretical limit of 2.29-2.89, when the gene for endonuclease V has been inserted into xeroderma pigmentosum cells and the enzyme is produced endogenously, as described by K. Valerie et al. in their 1987 CANCER RESEARCH paper referred to above.

No toxicity was observed in the unirradiated cells treated with liposomes. Survival in these cells ranged between 87% and 123% compared to cells not treated with liposomes.

Although specific embodiments of the invention have been described and illustrated, it is to be understood that modifications can be made without departing from the invention's spirit and scope. For example, although the invention has been illustrated in terms of DNA damage caused by ultraviolet light, it is equally applicable to DNA damage resulting from other sources, such as ionizing radiation, chemicals producing covalent adducts to DNA, and other deformations of bases or strand breaks. Similarly, in addition to being used after DNA damage has occurred, as in the examples presented above, liposomes containing DNA repair enzymes can be administered prophylactically prior to the time cells will be exposed to conditions under which DNA damage is likely.

TABLE 1

| Liposome | optical density | enzyme ug/ml | concentration units/ml |
|---|---|---|---|
| PC/DCP/Chol | 7.5 | 5.2 | 1,500 |
| PC/SA/Chol | 4.8 | 4.9 | 6,600 |

TABLE 2

| Treatment | Number Average Mol Wt (bases) | Breaks per million bases |
|---|---|---|
| none | 16,117 | 62.0 |
| DPPC/PC/Chol | 12,381 | 80.8 |
| DPPC/PC/Chol + Endonuclease V | 2,906 | 344.0 |

TABLE 3

| Cells Treated | UV J/m$^2$ | OD Liposome | Percent Control |
|---|---|---|---|
| XP12BE | 100 | 0 | 100 |
|  |  | 0.13 | 117 |
|  |  | 0.26 | 144 |
|  |  | 0.65 | 182 |
|  | 0 | 0 | 100 |
|  |  | 0.13 | 100 |
|  |  | 0.26 | 96 |
|  |  | 0.65 | 95 |
| Normal Human Epidermal Keratinocytes | 100 | 0 | 100 |
|  |  | 0.13 | 106 |
|  |  | 0.26 | 123 |
|  |  | 0.65 | 125 |

TABLE 4

| Liposome Treatment | Slope | Correlation Coefficient | Fluence Reduction Factor |
|---|---|---|---|
| none | −0.061 | 0.95 |  |
|  |  |  | 2.05 |
| DPPC/PC/Chol | −0.030 | 0.96 |  |
| none | −0.043 | 0.99 |  |
|  |  |  | 1.57 |
| PC/DCP | −0.027 | 0.95 |  |

What is claimed is:

1. A process for purifying a DNA repair enzyme comprising:

(a) contacting an aqueous solution of the DNA repair enzyme in an impure state with a molecular sieve, said DNA repair enzyme having a molecular weight in the range from about 16,500 daltons to about 19,000 daltons and said molecular sieve having an exclusion limit which is larger than about twice the molecular weight of the DNA repair enzyme and smaller than the molecular weight of at least some of the impurities in the aqueous solution such that the DNA repair enzyme will pass through the molecular sieve at a slower rate than at least some of said impurities;

(b) isocratically eluting the DNA repair enzyme from the molecular sieve with an aqueous elution solution so as to obtain the DNA repair enzyme in one or more selected fractions of the eluate in a state of enhanced purity, said aqueous elution solution being chosen so that complexes can form between the DNA repair enzyme and selectee deoxyribonucleic acids;

(c) without further purification, contacting the one or more selected fractions of step (b) in said aqueous elution solution with one or more selected deoxyribonucleic acids which have been immobilized on a solid support so as to form immobilized deoxyribonucleic-acid/DNA-repair-enzyme complexes between the DNA repair enzyme and the one or more selected, immobilized deoxyribonucleic acids;

(d) washing the immobilized complexes to remove at least some of the remaining impurities; and (e) eluting the DNA repair enzyme from the one or more selected, immobilized deoxyribonucleic acids so as to obtain the DNA repair enzyme in one or more selected fractions of the eluate in a state of further enhanced purity.

2. The process of claim 1 wherein the exclusion limit of the molecular sieve is (i) larger than about twice the Stokes' radius of the DNA repair enzyme and (ii) smaller than the Stokes' radius of at least some of the impurities.

3. The process of claim 2 wherein the exclusion limit of the molecular sieve is smaller than about 35 Angstroms.

4. The process of claim 1 wherein the exclusion limit of the molecular sieve is smaller than about 60,000 daltons.

5. The process of claim 1 wherein the molecular sieve comprises a gel filtration column.

6. The process of claim 1 wherein the deoxyribonucleic acids are single-stranded deoxyribonucleic acids.

7. The process of claim 1 wherein the selected, immobilized deoxyribonucleic acids comprise, a deoxyribonucleic acid affinity column.

8. The process of claim 1 wherein the DNA repair enzyme is eluted from the one or more selected, immobilized deoxyribonucleic acids using an aqueous elution solution which contains a gradient of a material capable of disassociating the DNA repair enzyme from the one or more selected, immobilized deoxyribonucleic acids.

9. The process of claim 8 wherein the material is selected from the group consisting of salts, acids, detergents, and competing ligands.

10. The process of claim 1 wherein the DNA repair enzyme is a homogeneous protein at the end of step (e) as determined by SDS polyacrylamide gel electrophoresis.

11. The process of claim 1 wherein the aqueous solution of the DNA enzyme in an impure state is obtained by (i) disrupting cells containing the DNA repair enzyme, (II) removing cell debris, and (iii) collecting the resulting solution, said solution comprising the aqueous solution of the DNA enzyme in an impure state.

12. The process of claim 1 wherein the aqueous solution of the DNA enzyme in an impure state is obtained by (i) disrupting cells containing the DNA repair enzyme, (ii) centrifuging the disrupted cells, (iii) collecting the supernatant, (iv) precipitating the proteins in the supernatant, and (v) resuspending the precipitate in the aqueous elution solution used to elute the DNA repair enzyme from the molecular sieve, said resuspended precipitate comprising the aqueous solution of the DNA enzyme in an impure state.

13. The process of claim 12 wherein prior to being contacted with the molecular sieve, the resuspended precipitate of step (v) is dialyzed against the aqueous elution solution used to elute the DNA repair enzyme from the molecular sieve.

14. The process of claim 12 wherein the nucleic acids from the disrupted cells are precipitated prior to centrifugation step (ii).

15. The process of claim 1 wherein the DNA repair enzyme is selected from the group consisting of T4 endonuclease V and $O^6$-methylguanine-DNA methyltransferase.

16. A process for producing a liposome-encapsulated DNA repair enzyme comprising:

(a) growing cells which synthesize the DNA repair enzyme, said DNA repair enzyme having a molecular weight in the range from about 16,500 daltons to about 19,000 daltons;

(b) preparing an extract of the cells which contains the DNA repair enzyme in an impure state;

(c) contacting the extract with a molecular sieve having an exclusion limit which is larger than about twice the molecular weight of the DNA repair enzyme and smaller than the molecular weight of at least some of the impurities in the extract such that the DNA repair enzyme will pass through the molecular sieve at a slower rate than at least some of said impurities;

(d) isocratically eluting the DNA repair enzyme from the molecular sieve with an aqueous elution solution so as to obtain the DNA repair enzyme in one or more selected fractions of the eluate in a state of enhanced purity, said aqueous elution solution being chosen so that complexes can form between the DNA repair enzyme and selected deoxyribonucleic acids;

(e) without further purification, contacting the one or more selected fractions from step (d) in said aqueous elution solution with one or more selected dioxyribonucleic acids which have been immobilized on a solid support so as to form immobilized deoxyribonucleic-acid/DNA-repair-enzyme complexes between the DNA repair enzyme and the one or more selected, immobilized deoxyribonucleic acids;

(f) washing the immobilized complexes to remove at least some of the remaining impurities;

(g) eluting the DNA repair enzyme from the one or more selected, immobilized deoxyribonucleic acids so as to obtain the DNA repair enzyme in one or more selected fractions of the eluate in a state of further enhanced purity; and (h) encapsulating at least a portion of the purified DNA repair enzyme contained in the one or more selected fractions of step (g) in liposomes.

17. The process of claim 16 wherein the exclusion limit of the molecular sieve is (i) larger than about twice the Stokes' radius of the DNA repair enzyme and (ii) smaller than the Stokes' radius of at least some of the impurities and wherein the molecular sieve comprises a gel filtration column.

18. The process of claim 17 wherein the exclusion limit of the molecular sieve is smaller than about 35 Angstroms.

19. The process of claim 16 wherein the exclusion limit of the molecular sieve is smaller than about 60,000 daltons.

20. The process of claim 16 wherein the one or more selected deoxyribonucleic acids are single-stranded deoxyribonucleic acids.

21. The process of claim 16 wherein the DNA repair enzyme is eluted from the one or more selected, immobilized deoxyribonucleic acids using an aqueous elution solution which contains a gradient of a material capable of disassociating the DNA repair enzyme from the one or more selected, immobilized deoxyribonucleic acids.

22. The process of claim 16 wherein the DNA repair enzyme is a homogeneous protein at the end of step (g)

as determined by SDS polyacrylamide gel electrophoresis.

23. The process of claim 16 wherein the DNA repair enzyme is T4 endonuclease V.

24. A composition comprising liposomes having the DNA repair enzyme T4 endonuclease V encapsulated therein.

25. The composition of claim 31 prepared by the process of claim 23.

* * * * *

UNITED STATES PATENT AND TRADEMARK OFFICE
CERTIFICATE OF CORRECTION

PATENT NO. : 5,077,211
DATED : December 31, 1991
INVENTOR(S) : Daniel B. Yarosh

It is certified that error appears in the above-identified patent and that said Letters Patent is hereby corrected as shown below:

Column 23, line 46    "(II)" should read "(ii)"

Column 26, line 3     "31" should read "24"

Signed and Sealed this

First Day of June, 1993

Attest:

MICHAEL K. KIRK

Attesting Officer    Acting Commissioner of Patents and Trademarks